US010849601B2

(12) United States Patent
Krueger et al.

(10) Patent No.: US 10,849,601 B2
(45) Date of Patent: Dec. 1, 2020

(54) METHODS AND APPARATUSES FOR REDUCING THE SOUND PROFILE OF BIOPSY DEVICES

(71) Applicant: MERIT MEDICAL SYSTEMS, INC.

(72) Inventors: John Krueger, San Diego, CA (US); Michael Plishka, Lake Villa, IL (US); Nathan Retzlaff, San Diego, CA (US)

(73) Assignee: Merit Medical Systems, Inc., South Jordan, UT (US)

( * ) Notice: Subject to any disclaimer, the term of this patent is extended or adjusted under 35 U.S.C. 154(b) by 580 days.

(21) Appl. No.: 15/244,872

(22) Filed: Aug. 23, 2016

(65) Prior Publication Data
US 2018/0055493 A1    Mar. 1, 2018

(51) Int. Cl.
*A61B 10/02*    (2006.01)
*B25F 5/00*    (2006.01)

(52) U.S. Cl.
CPC .. *A61B 10/0275* (2013.01); *A61B 2010/0208* (2013.01); *A61M 2205/42* (2013.01); *B25F 5/00* (2013.01)

(58) Field of Classification Search
CPC ....... A61B 10/0275; A61B 2010/0208; A61M 2205/42
See application file for complete search history.

(56) References Cited

U.S. PATENT DOCUMENTS

| | | | |
|---|---|---|---|
| 5,195,533 A | 3/1993 | Chin et al. | |
| 5,228,851 A | 7/1993 | Burton | |
| 5,578,050 A * | 11/1996 | Webb | A61B 17/3211 16/421 |
| 5,643,220 A | 7/1997 | Cosme | |
| 5,899,886 A * | 5/1999 | Cosme | A61M 5/3243 604/192 |
| 5,951,489 A | 9/1999 | Bauer | |
| 6,106,484 A | 8/2000 | Terwilliger | |
| RE46,135 E * | 9/2016 | Hibner | A61B 10/0096 |
| 2002/0082477 A1* | 6/2002 | Kim | A61B 1/00142 600/186 |
| 2004/0097831 A1* | 5/2004 | Bourne | A61B 10/0266 600/564 |

(Continued)

OTHER PUBLICATIONS

International Search Report and Written Opinion of related International Patent Application No. PCT/US2017/047387 dated Jan. 12, 2018.

(Continued)

*Primary Examiner* — Sean P Dougherty
(74) *Attorney, Agent, or Firm* — Stoel Rives LLP

(57) ABSTRACT

A device and method for dampening a biopsy device externally or internally. One variation of the external dampening device includes a flexible sleeve provided to cover external surfaces of the biopsy device. The dampening device may also include a device to cover the entire device externally, wherein only a needle portion is exposed. Further in another aspect, a spring constant or spring property of the springs used in the biopsy device may be altered to decrease the noise emitted from the biopsy device. A device and method is also disclosed for dampening a biopsy device internally using an elastic damper at the end portions of any springs that may be used in the biopsy device or at the end of a stroke of certain movable portions inside the biopsy device.

19 Claims, 19 Drawing Sheets

(56) References Cited

U.S. PATENT DOCUMENTS

| | | | |
|---|---|---|---|
| 2006/0155210 A1 | 7/2006 | Beckman et al. | |
| 2007/0032743 A1* | 2/2007 | Hibner | A61B 10/0283 600/566 |
| 2007/0239067 A1* | 10/2007 | Hibner | A61B 10/0041 600/567 |
| 2007/0255174 A1* | 11/2007 | Hibner | A61B 10/0275 600/567 |
| 2010/0298736 A1* | 11/2010 | Levy | A61B 10/0283 600/566 |
| 2011/0125104 A1* | 5/2011 | Lynn | A61M 39/045 604/256 |
| 2012/0215130 A1 | 8/2012 | Field et al. | |
| 2012/0270662 A1* | 10/2012 | Wakitani | A63F 13/02 463/47 |
| 2015/0148704 A1 | 5/2015 | Swick et al. | |
| 2015/0315564 A1* | 11/2015 | Kindt | A61B 50/00 600/572 |

OTHER PUBLICATIONS

European Search Report dated Feb. 21, 2020 for EP17844168.9.

* cited by examiner

METHODS AND APPARATUSES FOR REDUCING THE SOUND PROFILE OF BIOPSY DEVICES

FIELD OF THE INVENTION

Aspects of the disclosure relate generally to the field of biopsy devices, and particularly to dampening and/or reducing the noise emitted from biopsy devices.

BACKGROUND

Biopsies are commonly performed with biopsy devices that use suction or a force supplied by spring or similar biasing member. Soft tissue biopsies are commonly performed with spring loaded biopsy devices. A spring loaded biopsy device typically includes a needle comprising a stylet and a cannula. The stylet may include a side notch, and the cannula may include a cutting portion. The stylet and cannula may be coaxially arranged and extend axially along a longitudinal axis, with a free end designed to be inserted into the biopsy area; the opposite end is connected to a handpiece. The handpiece may include a charging portion for charging either one of or both the stylet and cannula. The handpiece may further include a single or plurality of buttons for triggering the release of any one of or both the cannula or stylet. Internally, the handpiece may include a stylet slider guided lengthwise inside the handpiece and connected to the stylet. A cannula slider may be guided lengthwise inside the handpiece and may be connected to the cannula. A biasing portion may elastically load the stylet and/or the cannula; the cannula and/or stylet may be charged though a user pulling or pressing on a lever or handle portion, or rotating a rotatable portion of the charging portion which compresses any one of the abovementioned elastic biasing portions. The handpiece may further include a holding and releasing portion provided to hold the stylet slider and the cannula slider in the loaded position and to release the cannula and/or stylet automatically in succession and/or individually when a button is pressed by a user. When a user presses a trigger button the device is fired the spring tension is released, causing the advance of the abovementioned stylet and/or cutting cannula.

A common problem associated with typical biopsy devices is that they may be perceived to be excessively loud. Oftentimes the combination of anxiety felt by a patient during a biopsy procedure, the frequency of the sound emitted from the biopsy device, and/or the relative near proximity of the procedure to the patients ear, for example, may result in the firing of the biopsy device startling the patient. Since a biopsy procedure may be intended to closely target a specific suspicious tissue mass or lesion, accuracy is often paramount, and any movement of the patient reacting to noise emitted from the device may result in an insufficient sample or missed target requiring additional biopsies. Accordingly, there is a need to dampen and/or reduce the noise emitted from biopsy devices.

Further, for example, during a biopsy procedure, such as a breast biopsy for example, the needle, cannula and/or stylet may be positioned conjunction with use of ultrasound. Accordingly, ultrasound gel may be used to transition any sound waves from the ultrasound probe onto the skin. Frequently the abovementioned gel may transfer to a user's (e.g. a clinician's) hand or to the biopsy device and act as a lubricant making it difficult or cumbersome for the user of the biopsy device to property grip the handle of the biopsy device. Accordingly, there is a need to improve the tactile qualities of a biopsy device for both dry use and to improve a user's grip when a biopsy device may come into contact with fluids such as the abovementioned ultrasound gel.

SUMMARY

In accordance with one aspect of the present disclosure, a device and method is employed for dampening a biopsy device externally. The dampening device and method may include a flexible sleeve provided to cover external surfaces of the biopsy device. The device may also include a device to cover substantially or substantially all of a housing of the entire device externally, wherein only a needle portion and/or any moving external parts are exposed, for example. In another aspect of the disclosure, a spring constant or spring property of the springs to be used in the biopsy device may be altered to decrease the force applied when the device is fired. The decrease in force may be provided throughout the release of the spring, for example, or the force may be progressively reduced at a beginning or an end portion of the stroke of a part moved or driven by the spring. In accordance with another aspect of the disclosure, a device and method is disclosed for dampening a biopsy device internally using an elastic damper at the end portions of any springs that may be used in the biopsy device or at the end of a stroke of any movable portion inside the biopsy device.

Additional advantages and novel features of these aspects will be set forth in part in the description that follows, and in part will become more apparent to those skilled in the art upon examination of the following or upon learning by practice of the disclosure.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

DETAILED DESCRIPTION

Figure 1:
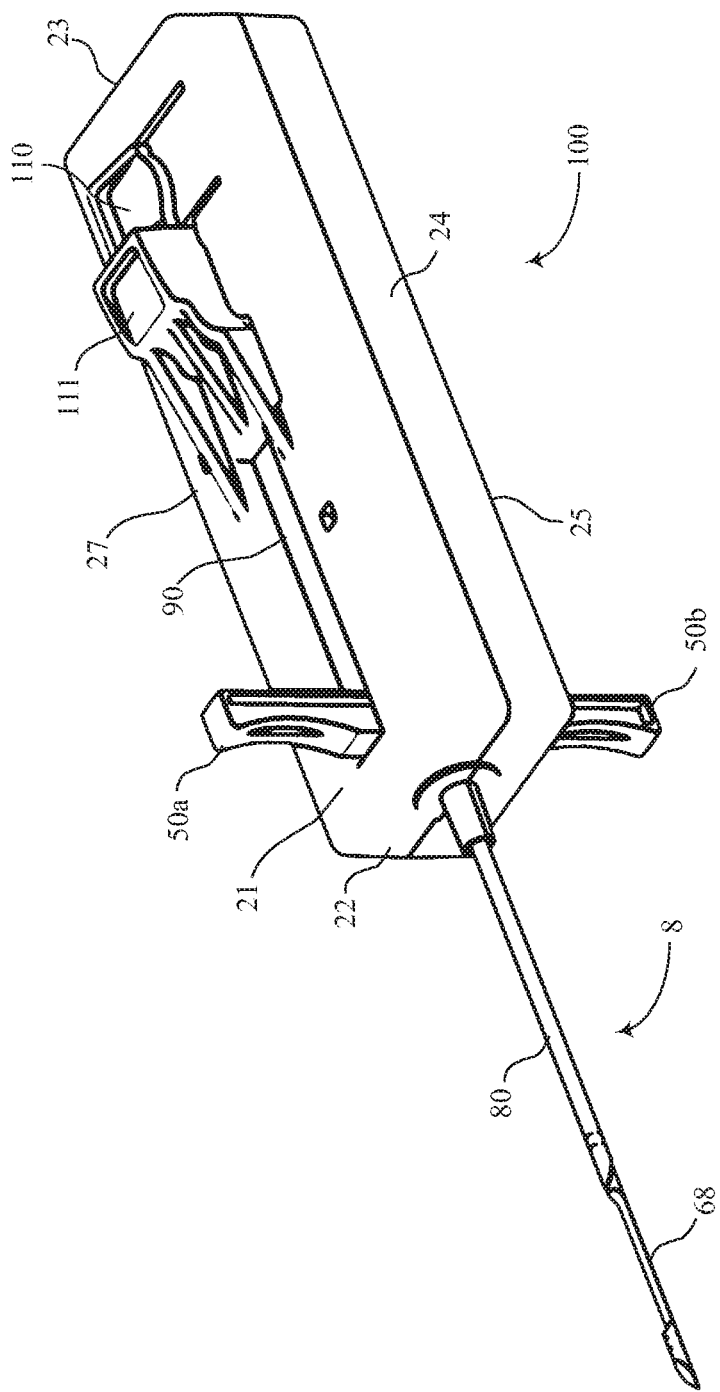
FIG. 1 is a perspective view depicting an example of a biopsy device for use with dampening features in accordance with one aspect of the present disclosure.

In connection with the views and examples of FIGS. 1-17, like numbers indicate corresponding elements. FIG. 1 shows a view of one example biopsy device 100 for use in accordance with aspects of the present invention.

The biopsy device 100 of FIG. 1 may include a needle 8, and the needle 8 may comprise a cannula 80 and a stylet 68, for example, that are coaxially arranged. It is noted that the term needle is not limited to a cannula and a stylet, as an alternative or in combination with a cannula and/or stylet, a needle may include an extension for subcutaneous delivery of fluids, a subcutaneous marker delivery extension and/or any similar known biopsy device for removal of subcutaneous tissue. The terms needle, stylet, cannula, biopsy extension or delivery extension are interchangeably used herein. As shown in the orientation of FIG. 1, the biopsy device 100 may include a first wall 22, a second wall 25, a third wall 21, a fourth wall 24, a fifth wall 27, and a sixth wall 23. The first wall 22 may include an opening for the passage of abovementioned needle 8. The second wall 25 may include a sliding channel (not shown in FIG. 1), for passing a loading device extension 50b as part of a charging portion for the device 100. The loading device extension 50b as shown in FIG. 1 is not limited to as shown and may include, for example, a recessed loading portion, a rotatable loading portion or a cocking pullback portion; the terms loading device extension, rotatable loading portion, recessed loading portion and/or cocking pullback portion may be interchangeably used herein. The third wall 21 may include a sliding channel 90, through which a loading device extension 50a may extend. The third wall 21 may also include a first trigger 110 and a second trigger 111, for example, for releasing the abovementioned cannula 80 and/or stylet 68. The first trigger 110 and/or second trigger 111 may release a biasing force imparted by a user through the loading device extensions 50a and/or 50b. A single or plurality of biasing members (not shown) internal to the biopsy device 100 may be connected to the cannula 80 and/or stylet 68. The abovementioned biasing member or members may be compressed by a biopsy device user by sliding the loading device extensions 50a and 50b in the abovementioned sliding channels 90 towards a sixth wall 23, for example. Once the biasing devices are held in a compressed state, the loading device extensions 50a and 50b may return to a portion of the sliding channel closest to a first wall 22. Triggers 110 and/or 111 may release the compressed biasing devices causing the cannula 80 and/or stylet to be released with a force sufficient to penetrate tissue for obtaining a tissue sample. U.S. Pat. No. 5,951,489 discloses one example of the operation of a biopsy appliance and is incorporated by reference herein.

Figure 16:
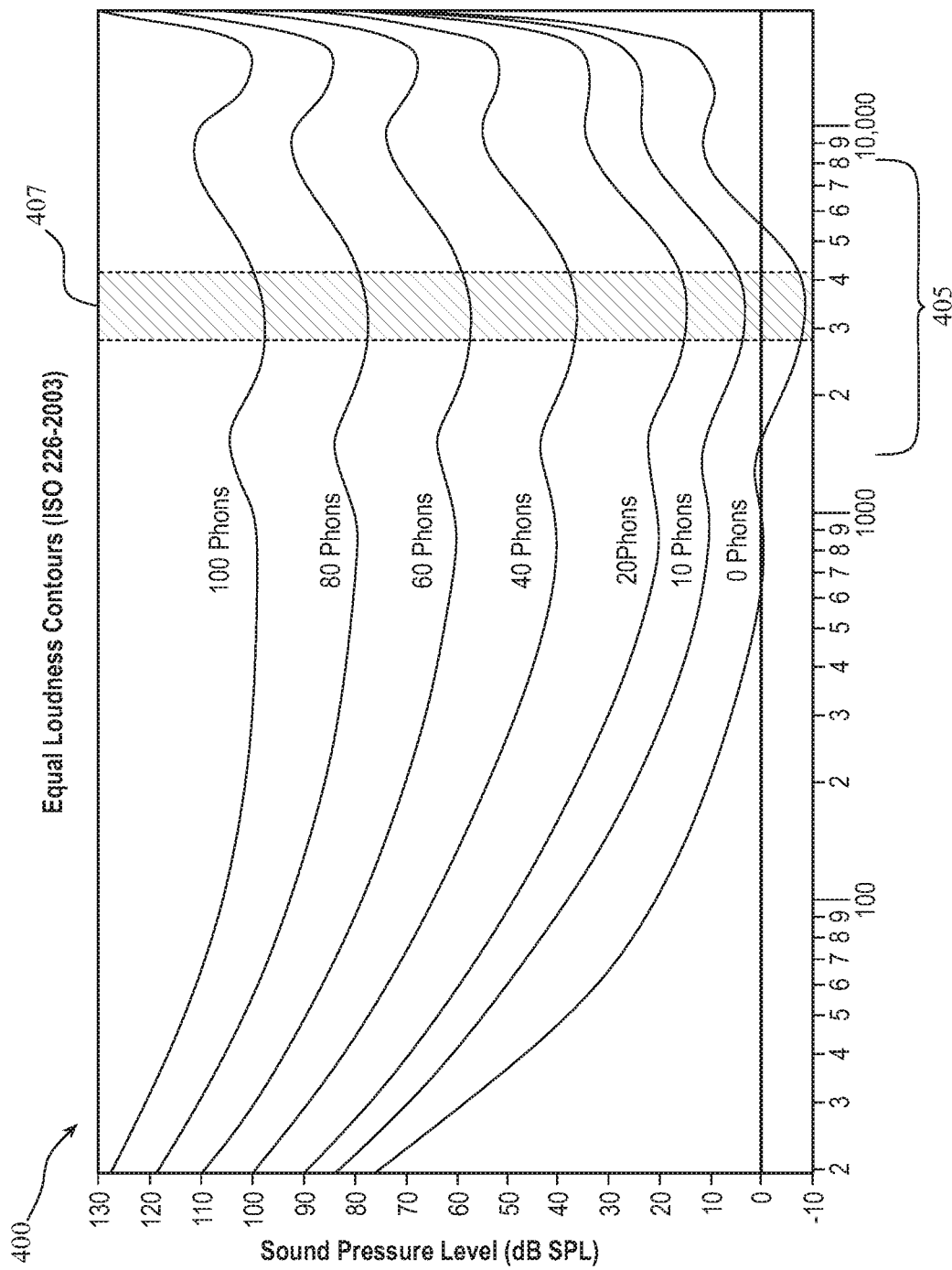
FIG. 16 is a chart depicting equal loudness contours for reference in accordance with one aspect of the present disclosure.

Noise disturbance from spring loaded biopsy devices may be attributed to the inherent sensitivity of the human ear, among other things, and the abovementioned biasing device release force and/or internal components of a biopsy device contacting other internal components and/or the outer case of the biopsy device may produce a noise in a range that is particularly problematic. The energy from internal components contacting the outer casing of the biopsy device may be dissipated though the propagation of vibrations as longitudinal and/or transverse waves, which may cause a resonance of the biopsy device. While not limited as such, the resonance frequency of the biopsy device may be found through the following formula (Formula 1):

$$f_n = \frac{v_a}{\lambda_n} = \frac{v_a n}{2L} \qquad \text{(Formula 1)}$$

where $v_a$ is the speed of sound in air, n is the mode of vibration, and L is the length of the biopsy device. In general, human hearing is based on a detection of changes in sound pressure. However, the human ear generally does not have a frequency response that is linearly related to frequency versus amplitude. International standard ISO 226:2003 sets forth the phon as a unit of loudness taking into consideration the effect of frequency on the perceived loudness of tones by humans. As shown in FIG. 16, ISO 226-2003 provides for Equal Loudness Contours, each contour represents a sound pressure over the frequency spectrum for which a human would generally perceive a constant loudness. The dip in phon curves 400 indicates the increase in sensitivity of the human ear to certain frequency ranges. As shown in FIG. 16, the human ear is particularly sensitive to frequencies in the shaded region 407, more specifically in the range of 3,000 to 4,000 Hz. In the 3,000 to 4,000 Hz frequency range, a person may perceive sounds as being as high as 10-20 dB louder than other frequencies. Thus, it may be advantageous to dampen vibration emitted from the biopsy device at the resonance frequency of a biopsy device; especially so as to be outside the abovementioned frequencies to which human ears are most sensitive.

In accordance with one aspect, a device and method may be employed for dampening a biopsy device externally. The dampening device and method may include a flexible sleeve provided either as a separate part or molded to the external surfaces of the device to cover the external surfaces of the biopsy device 100, for example. In connection with the views and examples of FIGS. 2-10, like numbers indicate the same or corresponding elements. FIGS. 1 and 7-9 show views of an example side loading biopsy device 100 and example dampening apparatus 101.

Referring now to FIGS. 2-9, dampening of an example biopsy device 100 may include the use of an example dampening device 101 at least partially covering the outer surfaces of the biopsy device 100. The example dampening device 101 may comprise an elastic material having a thickness 117. The elastic material for use with the example implementation is not limited to, and may include any one or combination of: a silicone rubber and/or a thermoplastic elastomer, which may include; a styrenic block copolymer, thermoplastic olefin, thermoplastic polyurethane, thermoplastic copolyester, and/or a thermoplastic polyamide. In one aspect, it may be advantageous to provide a material having a varied or varying durometer, such as an optimized or approximately optimized durometer for a particular application. For instance in a situation where a biopsy device is frequently used with ultrasound gel, a material having lower durometer may be used to provide a user (e.g. a clinician) with improved grip on the device. Further, it is also noted that, if a durometer of the dampening device is decreased below a preferred or ideal value, for example, the dampening device may stick to other materials contacting the dampening device (e.g. a clinicians gloves). In another aspect, the dampening device may be formed of a material having a durometer ranging from about 25 to 55 Shore (e.g., +/−5%), for example, when measured on an ASTM D2240 type A scale. In another aspect, the damping device may be formed of a material having a durometer ranging from about 35 to 45 Shore A (e.g., +/−5%).

The aforementioned materials or materials with similar qualities may be provided as a substrate having multiple layers of one or more of the above materials. Further, portions of the dampening device may be formed so as to have multiple layers corresponding to a portion of the outer surface of the biopsy device, wherein the multiple layers are only used on a portion of the biopsy device determined to emit the most vibration, or layers may be optimized so as to dampen certain frequencies on a portion of the outer surface of the biopsy device. Further, portions of the dampening device may be formed of a different material or a material having different material properties (e.g., differing durometer) based on a portion of the biopsy device the material is to contact, for example. Further, the abovementioned variations in materials or layers of materials may be selected to have preferred or optimized properties in order to correspond to tactile qualities desirable to the user (e.g. portions a clinician is most likely to come into direct contact with during a biopsy procedure). The elastic material may be molded separately from the biopsy device or may be molded directly onto the outer surfaces of the biopsy device. The dampening device may include several layers and may be formed as a substrate. The aforementioned dampening substrate may be permanently adhered to the outer surface or surfaces of the biopsy device, or may be adhered to the outer surface in a removable fashion as described below.

Figure 2:
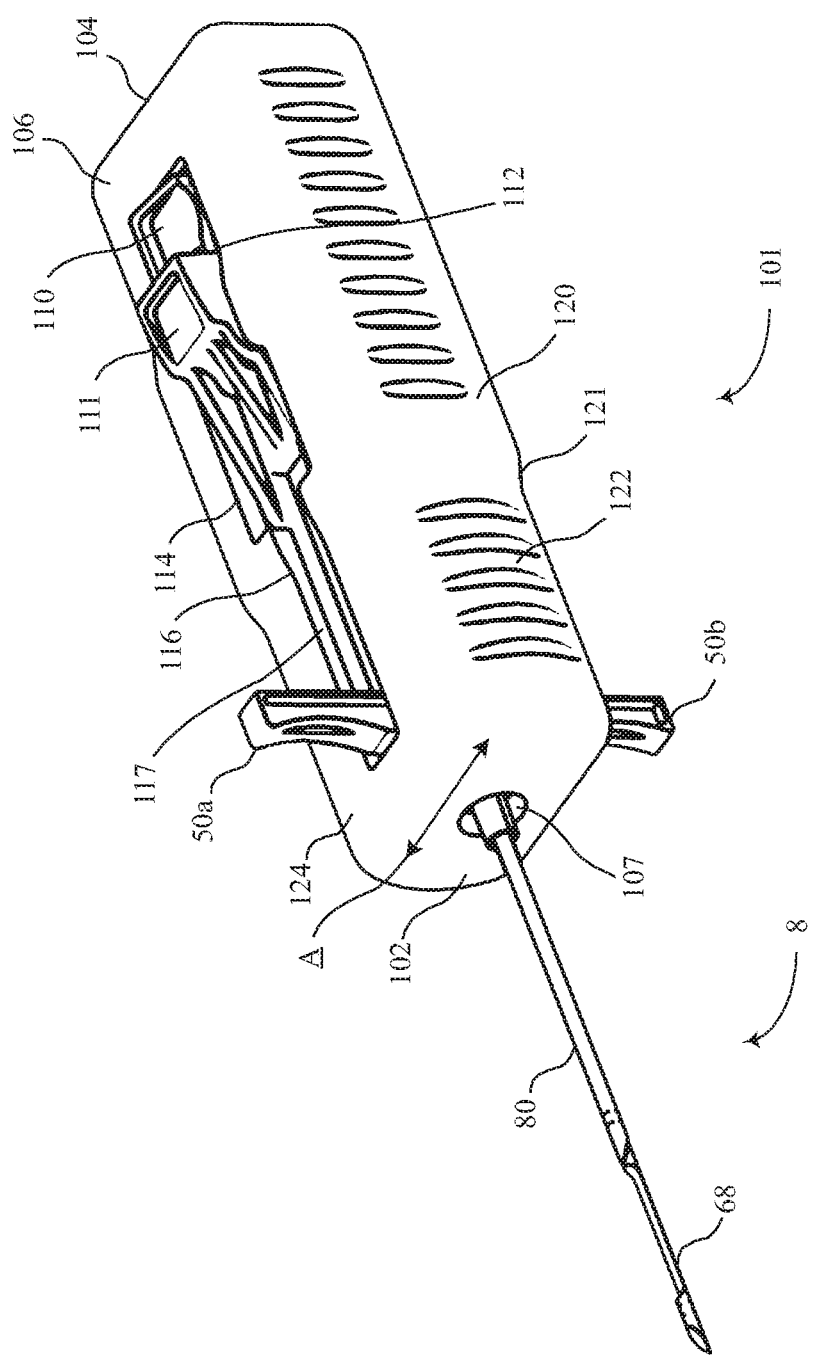
FIG. 2 is a perspective view depicting an example of a biopsy device having a dampening device installed in accordance with one aspect of the present disclosure.
Figure 3:
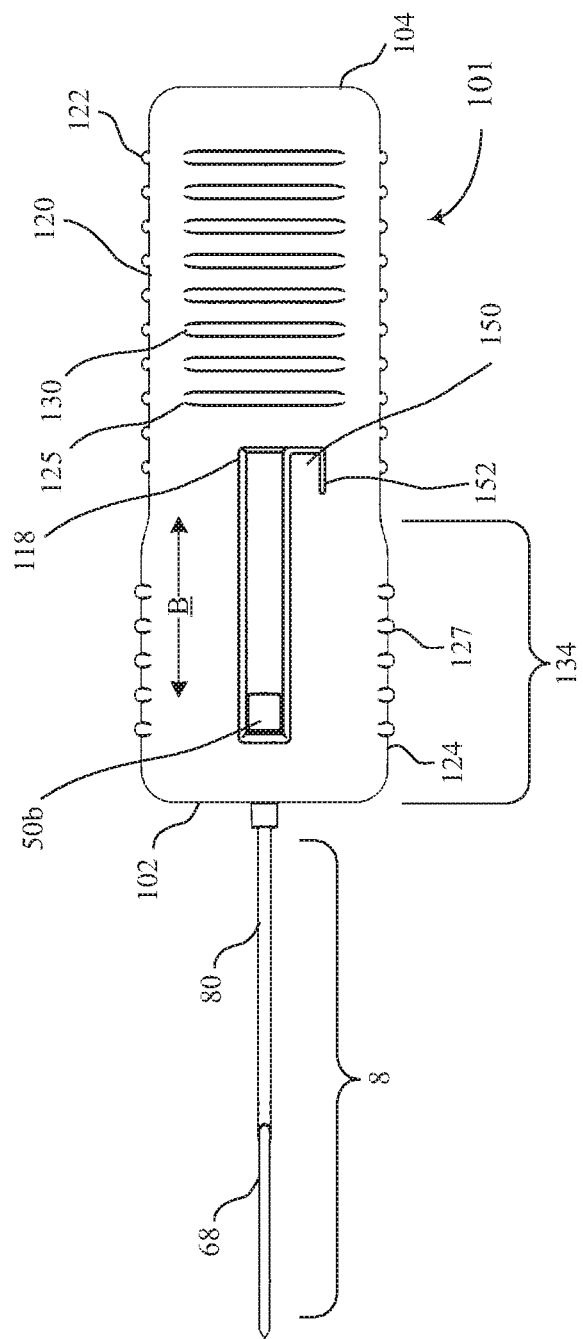
FIG. 3 is a bottom (when the device is oriented for use in a horizontal direction) view depicting an example of a biopsy device having a dampening device installed in accordance with one aspect of the present disclosure.
Figure 4:
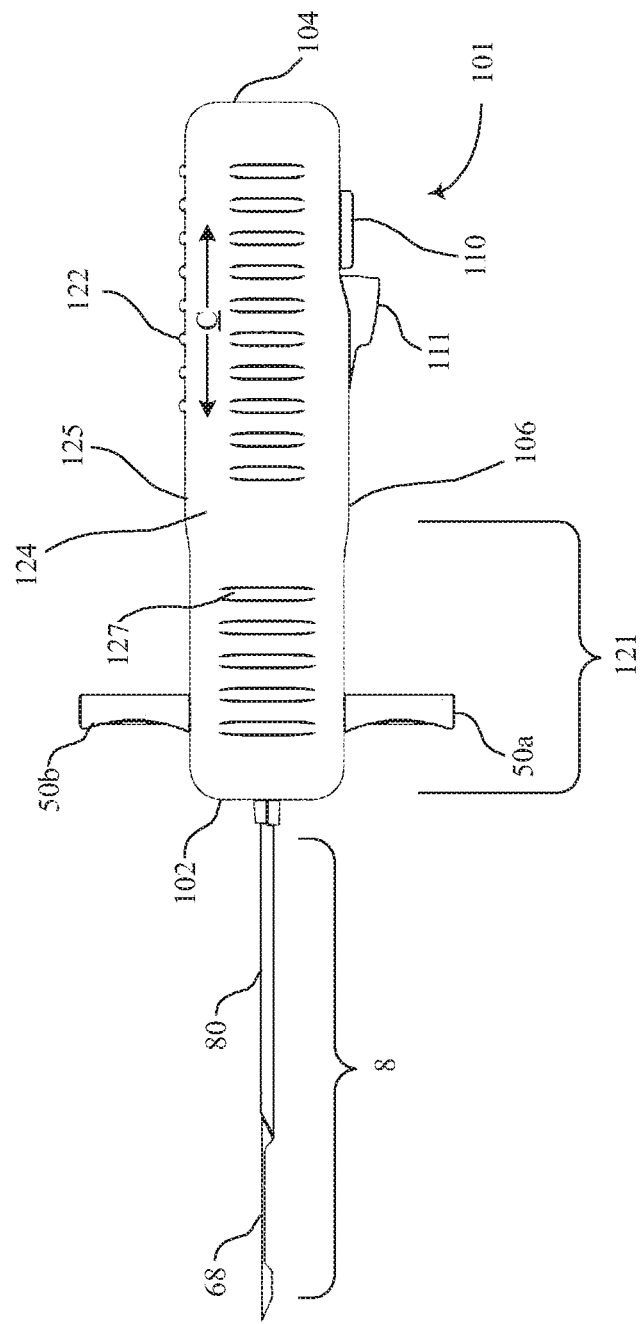
FIG. 4 is a side view of an example of the biopsy device of FIG. 3 having a dampening device installed in accordance with one aspect of the present disclosure.
Figure 5:
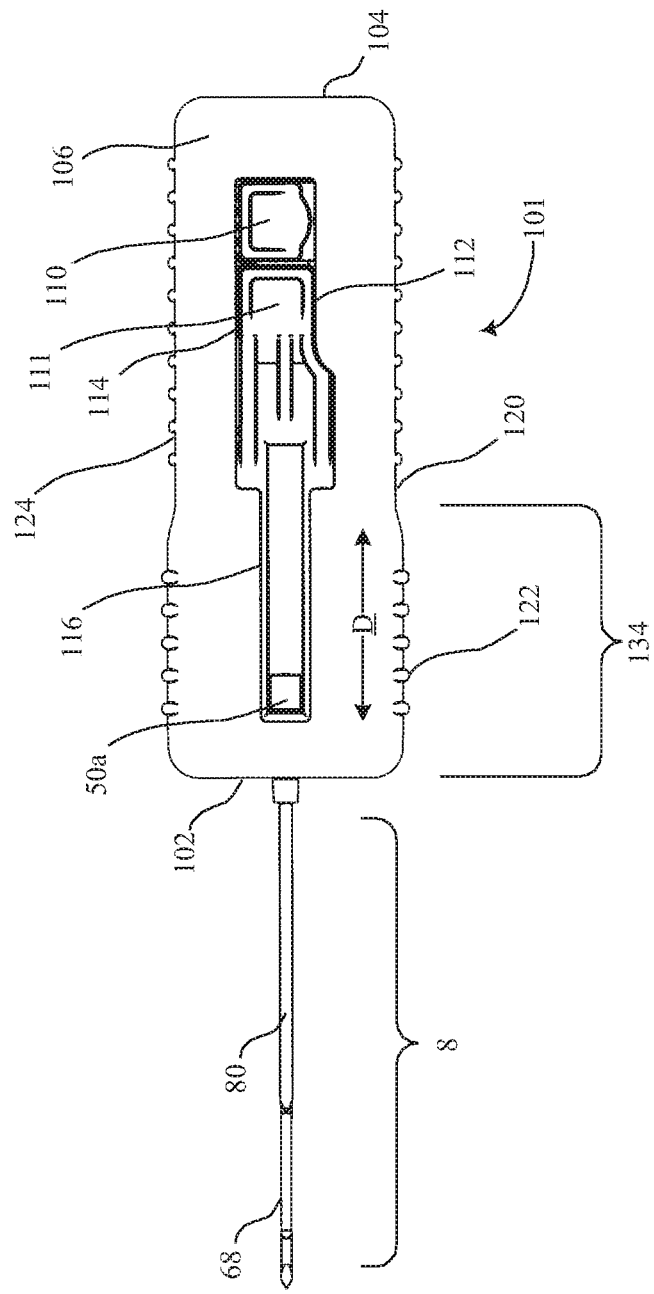
FIG. 5 is a top view depicting the example of a biopsy device of FIG. 3 having a dampening device installed in accordance with one aspect of the present disclosure.
Figure 6:
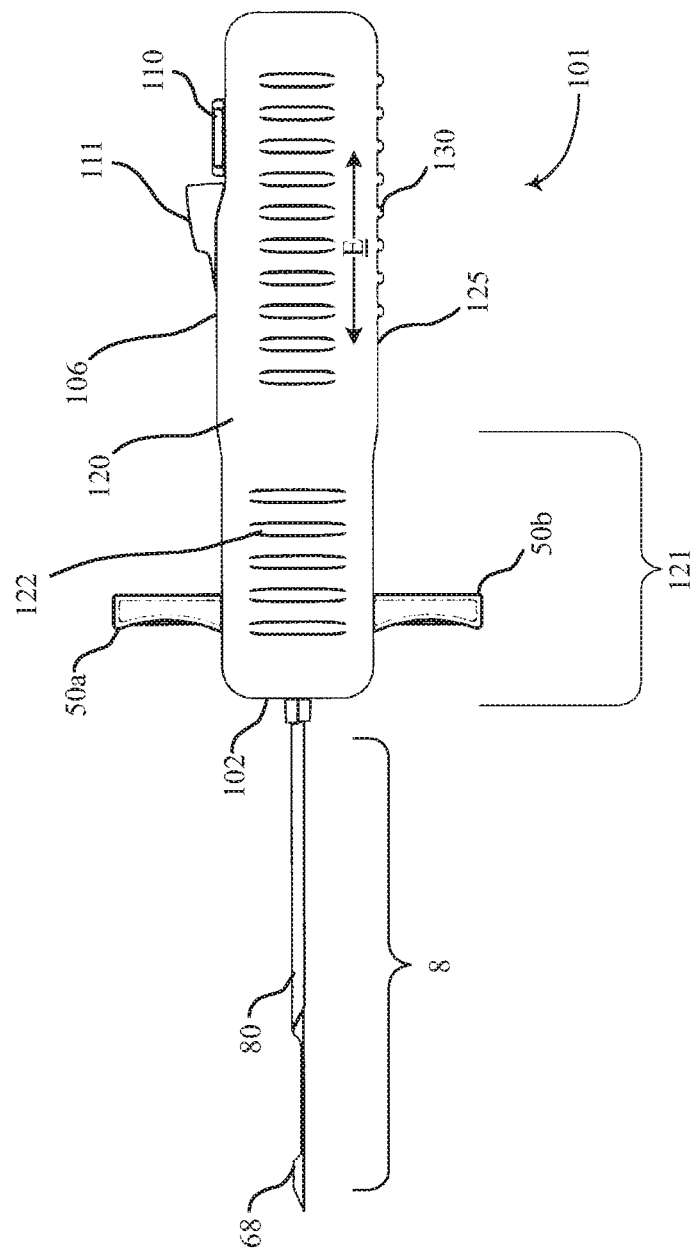
FIG. 6 is an opposite side view of the biopsy device of FIG. 4 having an example dampening device installed in accordance with one aspect of the current disclosure.
Figure 7:
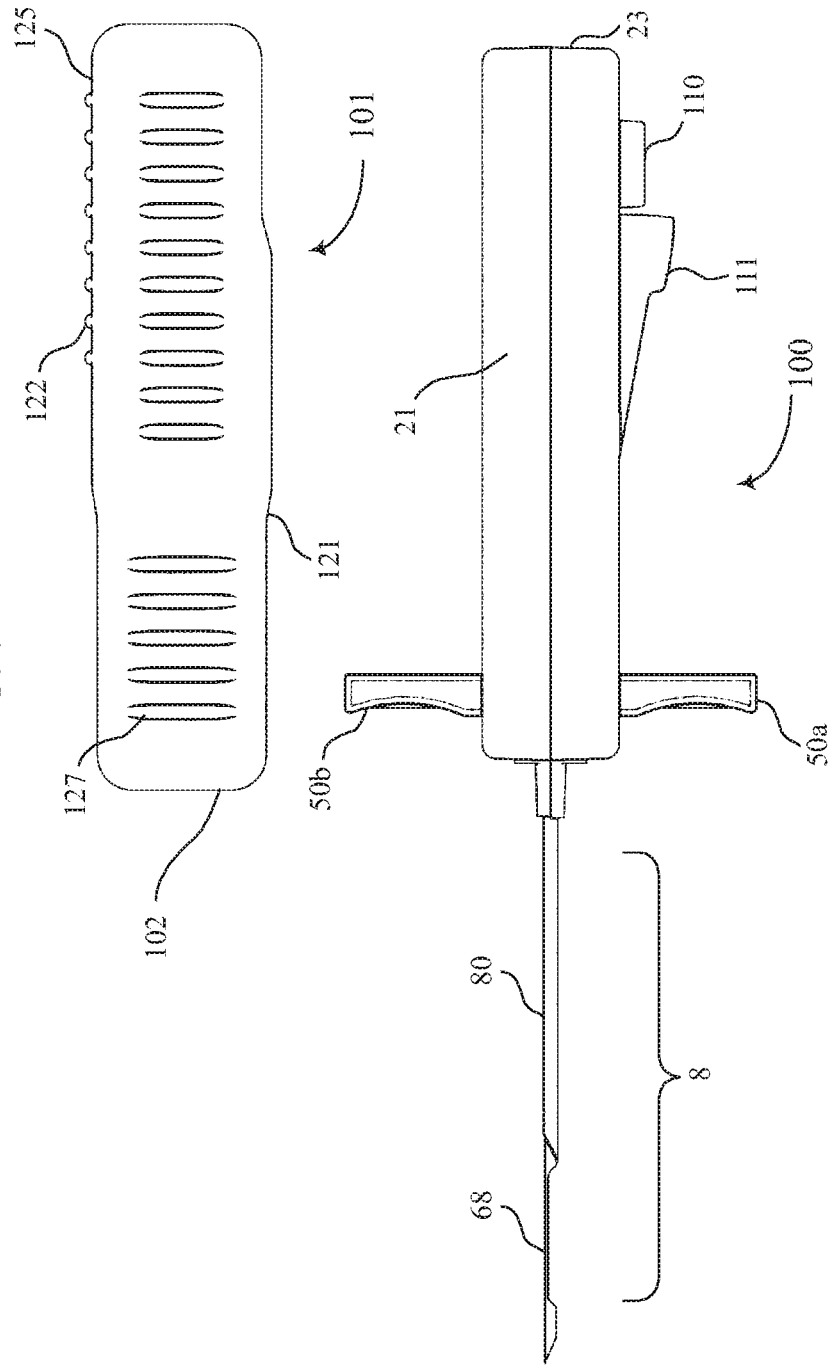
FIG. 7 is a side view (when the device is oriented for use in a horizontal direction) depicting an unassembled biopsy device and dampening device in accordance with one aspect of the current disclosure.
Figure 10:
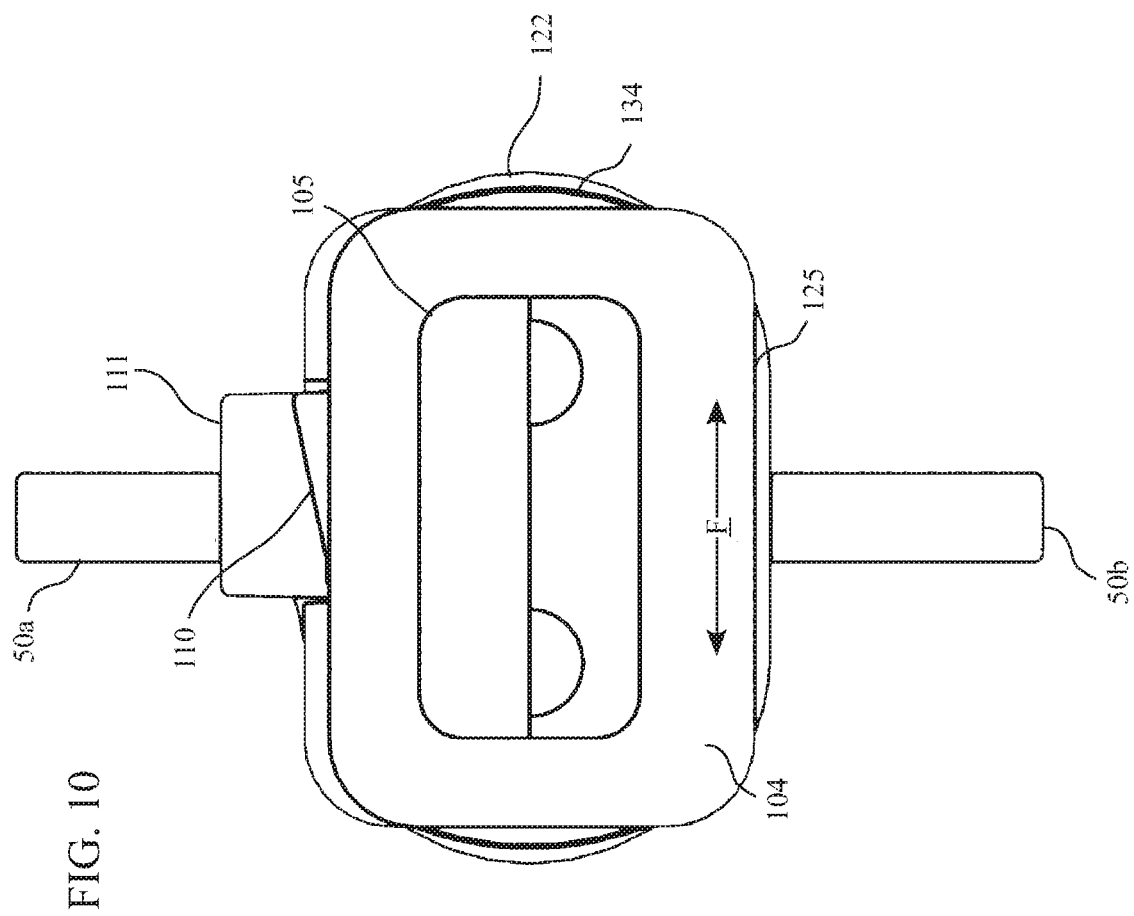
FIG. 10 is a rear view depicting the biopsy device and dampening device of FIG. 4, in accordance with one aspect of the current disclosure.
Figure 11:
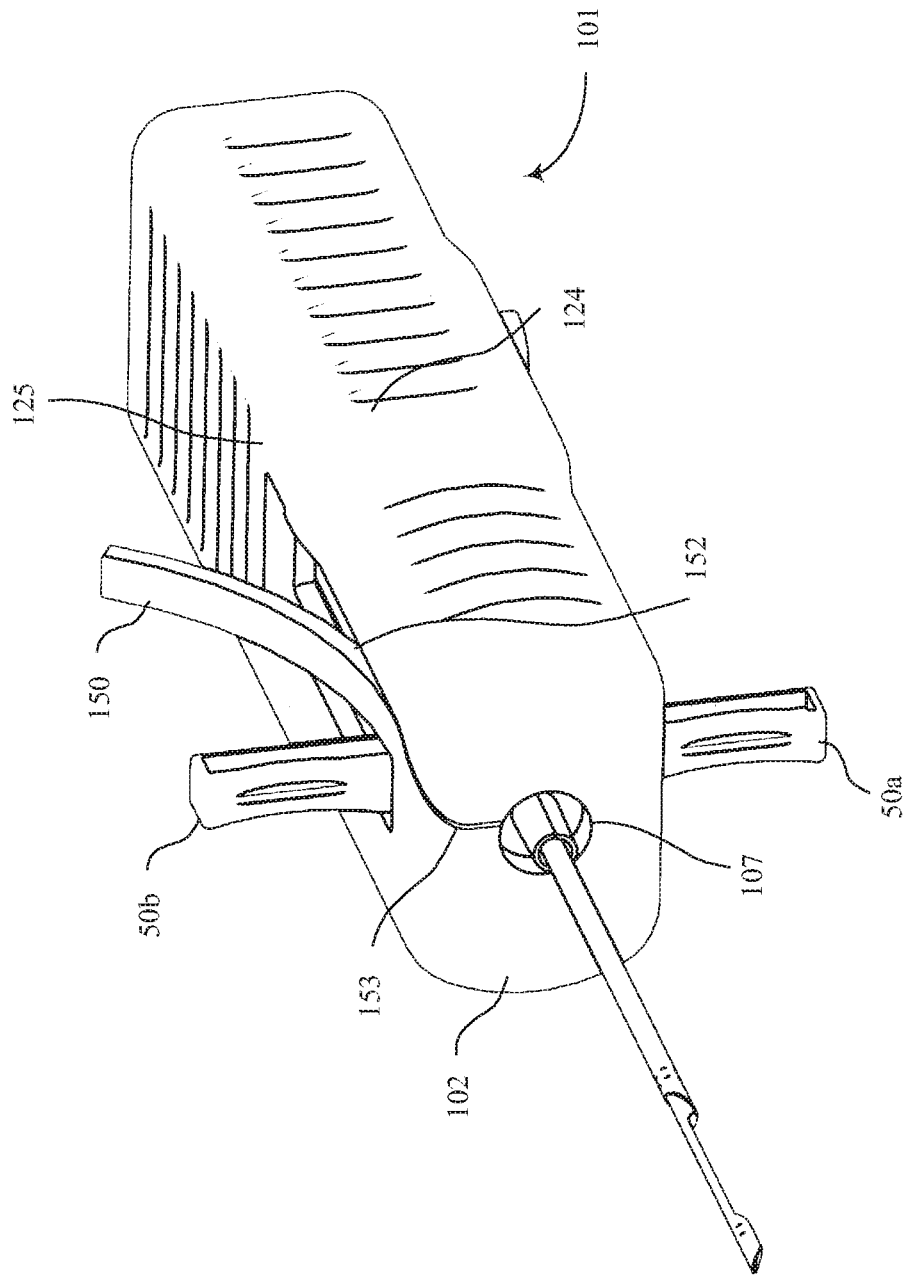
FIG. 11 Is a perspective view depicting an example of a biopsy device having a dampening device installed and showing a tab portion extended in accordance with one aspect of the present disclosure.
Figure 12:
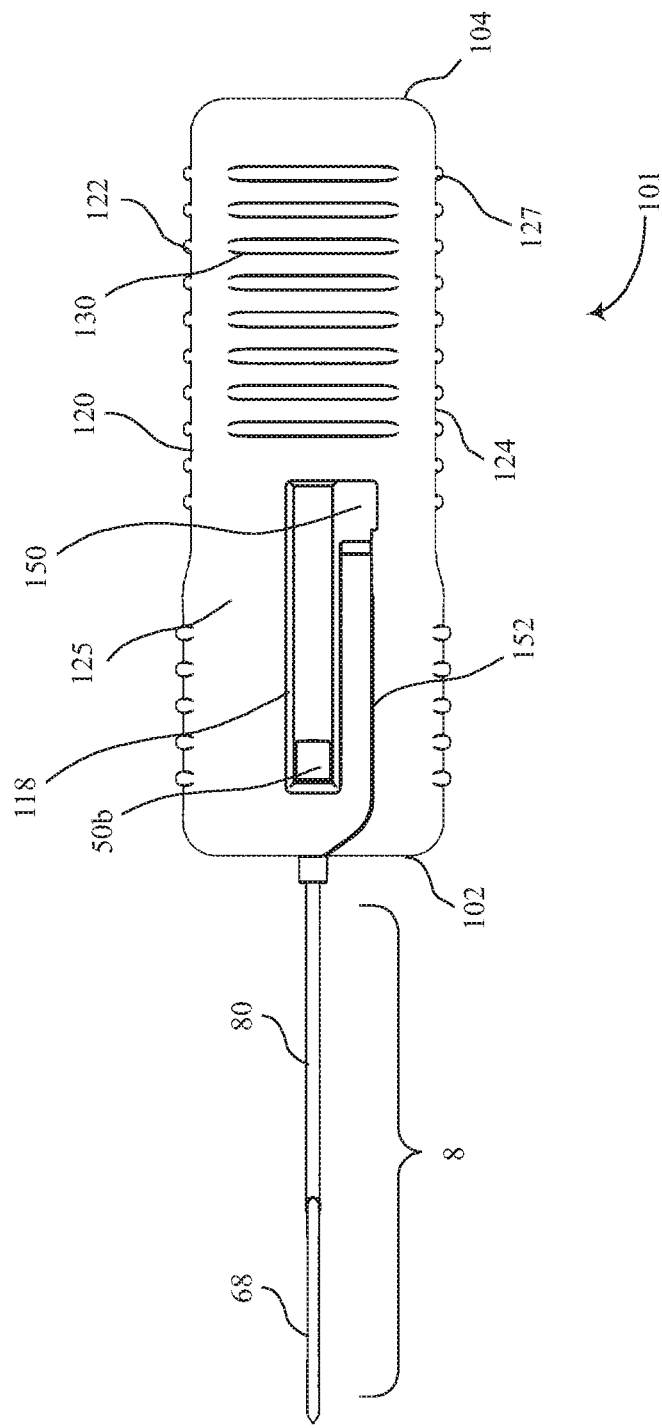
FIG. 12 is a top view depicting the example biopsy device having a dampening device of FIG. 11 installed in accordance with one aspect of the present disclosure.
Figure 13:
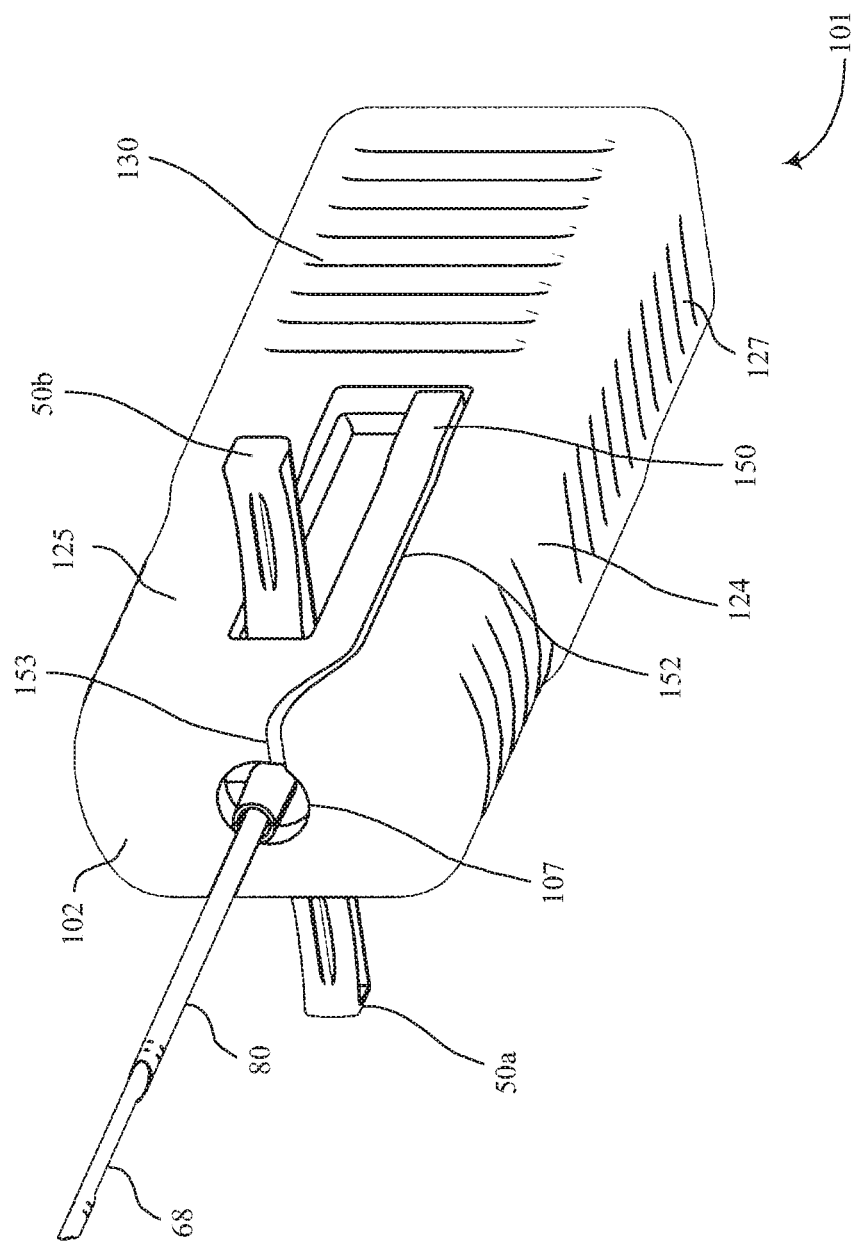
FIG. 13 is another perspective view depicting the example biopsy device having a dampening device of FIG. 11 installed in accordance with one aspect of the present disclosure.
Figure 14:
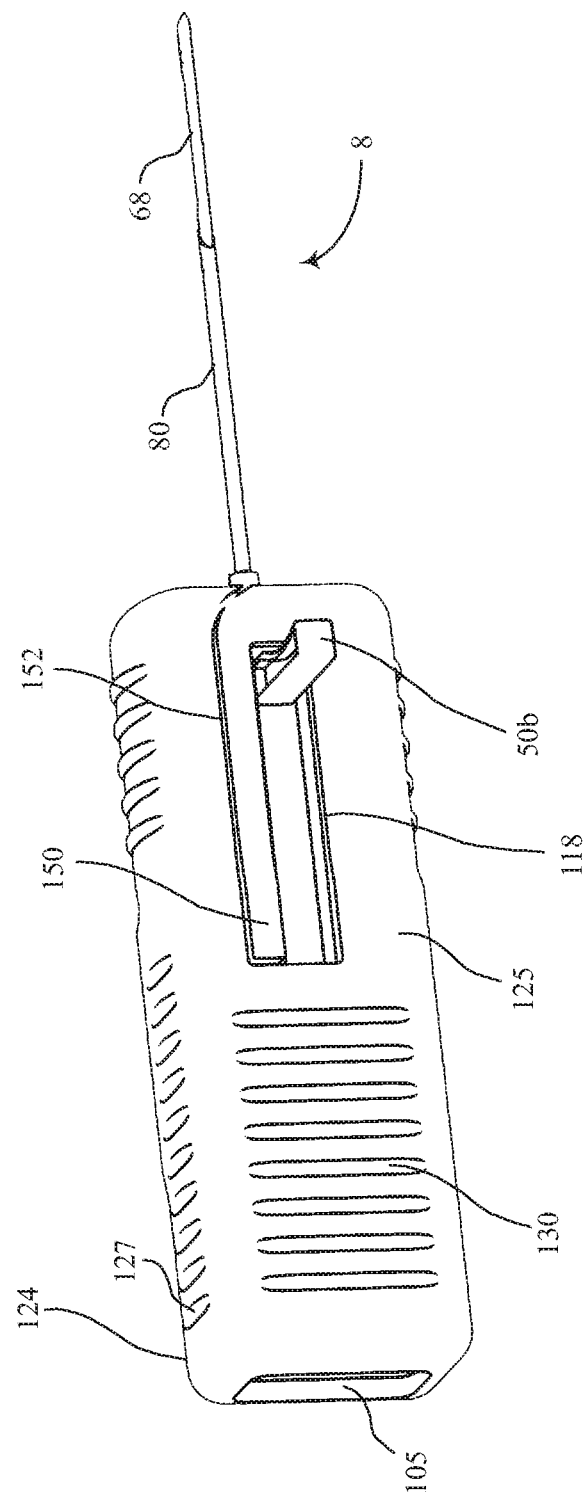
FIG. 14 show another view depicting the example of a biopsy device having a dampening device of FIG. 11 installed in accordance with one aspect of the present disclosure.
Figure 15:
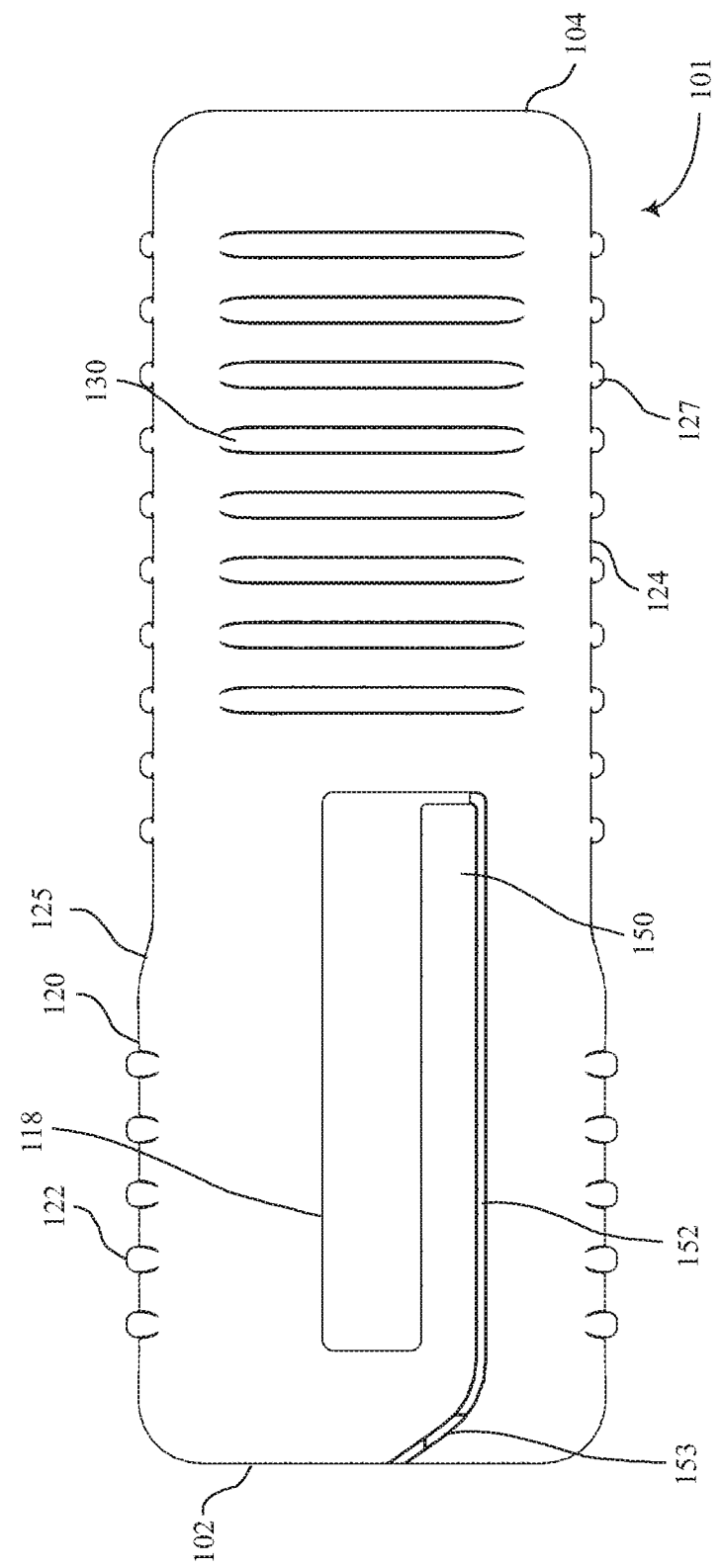
FIG. 15 is a bottom view depicting an example dampening device having a tab portion in accordance with one aspect of the present disclosure.

Referring to FIGS. 2 and 3, the dampening apparatus may include a first wall portion 102 having an opening 107 for allowing a biopsy needle 8 to pass therethrough. The dampening apparatus 101 may further include a second wall portion 125 having at least a portion of its longitudinally extending surface B lying in a plane that may be substantially perpendicular to a longitudinally extending surface A of the first wall portion 102. The second wall portion 125 may further include an opening 118 for allowing a loading device extension of a biopsy device 50b to pass therethrough. Referring to FIGS. 4 and 5, the dampening device 101 may include a third wall portion 106, the third wall portion 106 having at least one longitudinally extending surface D extending in a plane substantially parallel to a longitudinally extending surface B of the second wall portion 125 and perpendicular to a longitudinally extending surface A of the first wall portion 102. The third wall portion 106 may include an opening 116 for allowing a loading device extension 50a of the biopsy device to pass therethrough. Referring to FIGS. 2-4, the dampening apparatus may further include a fourth wall portion 120, a surface of the fourth wall portion 120 having at least a portion of its longitudinally extending surface E lying in a plane substantially perpendicular to planes lying in longitudinally extending surfaces of the first wall portion 102, the second wall portion 125, and the third wall portion 106. As shown in FIG. 4, the dampening apparatus 101 may include a fifth wall portion 124 having a longitudinally extending surface C lying at least partially in a plane substantially perpendicular to planes lying in longitudinally extending surfaces of the first wall portion 102, the second wall portion 125, and the third wall portion 106. As shown in FIG. 5, the plane lying in the longitudinally extending fifth wall portion 124 may also be substantially parallel to the longitudinally extending plane lying in a surface of the fourth wall portion 120. As shown in FIGS. 4, 6 and 10, sixth wall portion 104 may have a longitudinally extending surface F lying in a plane substantially perpendicular to planes lying in longitudinally extending surfaces of the second wall portion 125, the third wall portion 106, the fourth wall portion 120, and the fifth wall portion 124. A longitudinally extending surface F of the sixth wall portion 104 may also lie in a plane substantially parallel to a longitudinally extending surface A of the first wall portion 102.

Figure 8:
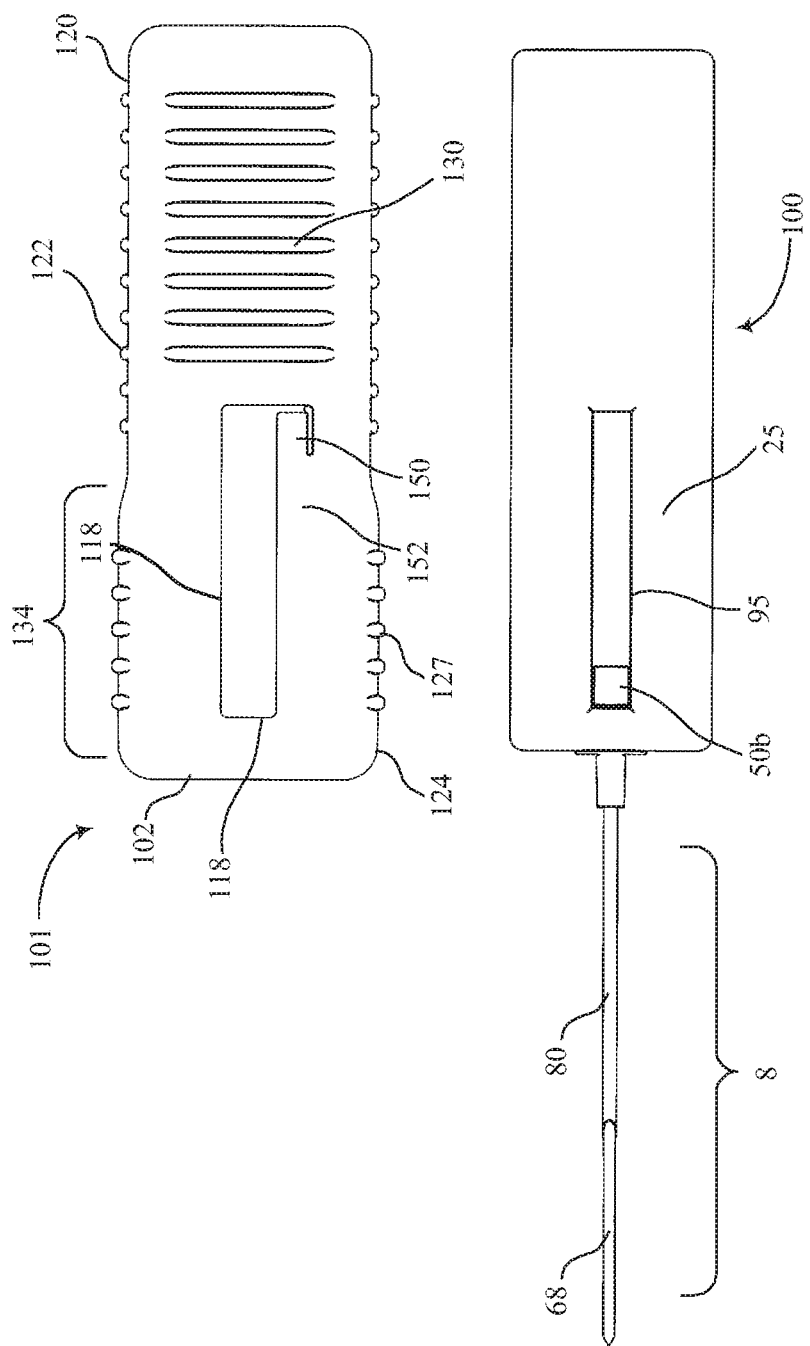
FIG. 8 is a bottom view depicting the unassembled biopsy device and dampening device of FIG. 7 and an uninstalled dampening device in accordance with one aspect of the current disclosure.

As shown in FIG. 3, the second wall portion 125 may include an opening 118 corresponding to the sliding channel (not shown in FIG. 3; see channel 95 on side 25 shown in FIG. 8) of the biopsy device 100. The minor axis width of opening 118 may be larger than or may be slightly smaller than the width of loading device extension 50b. Accordingly, the sides of opening 118 may be spaced from or may be in contact with the sides of the loading device extension 50b when the dampening device 101 is installed on the biopsy device 100. The second wall portion 125 may further include a tear open portion 152 terminating in a tab portion 150. The tab portion 150 may have a surface extending in a plane substantially parallel to a longitudinally extending plane of the second wall 125, so as to form a smooth surface with second wall 125. Alternatively, tab portion 150 may have a surface extending in a plane forming an angle in relation to the plane lying in a longitudinally extending surface of wall 125, such that the tab portion 150 protrudes from the surface of the second wall 125. The tear open portion 152 may have a reduced thickness and/or may include perforations as shown in FIG. 8. Further the tab portion 150 may include a textured surface to assist a user in grasping the tab portion 150, such as to initiate a tear. The second wall 125 may also or alternatively include a plurality of ridges 130, as shown in FIG. 6. Each of the ridges 130 may protrude from a surface of the second wall 125.

Figure 9:
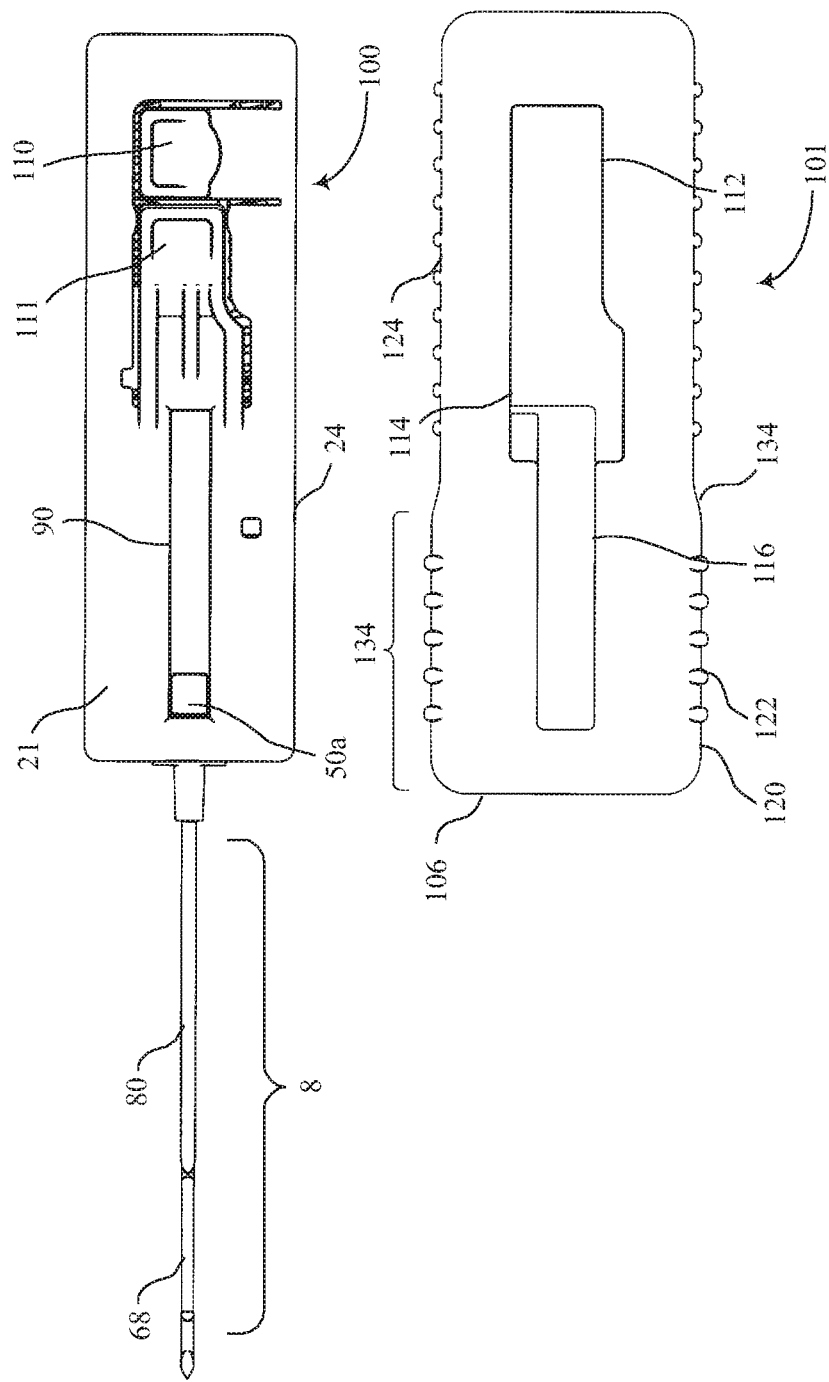
FIG. 9 is a top view depicting the unassembled biopsy device and dampening device of FIG. 7 in accordance with one aspect of the current disclosure.

As shown in FIGS. 2 and 5, the third wall portion 106 may include an opening 116 corresponding to the sliding channel 90 of the biopsy device 100, as shown in FIG. 9. The minor axis width of opening 116 may be larger than or may be slightly smaller than the width of loading device extension 50a. Accordingly, the opening 116 may be spaced from or may be in contact with the sides of the loading device extension 50a when the dampening device 101 is installed on the biopsy device 100. The third wall portion 106 may further include a second opening 114 in communication with opening 116 (or may otherwise constitute a portion of opening 116). The second opening/portion 114 may be dimensioned to allow a user of the biopsy device to engage a first trigger 110 and/or a second trigger 111. The second opening/portion 114 may further include a narrowed width portion 112 corresponding to the contours of trigger 110 and/or 111. Further the second opening/portion 114 may be dimensioned to allow for the removal of the dampening device from the biopsy device through openings 114 and 116, for example. The minor axis width of opening/portion 114 and/or 112 may be larger than or may be slightly smaller than the width of trigger 110 and/or 111. Accordingly, opening/portion 114 and/or 112 may be spaced from or may be in contact with the sides of the abovementioned triggers 110, 111 when the dampening device 101 is installed on the biopsy device 100. The dimensions of the abovementioned opening 116, opening/portion 114 and/or 112 may allow the installation of the biopsy device 100 in to the dampening device 101 through the abovementioned openings. The third wall 106 may also optionally include a plurality of ridges (not shown) similar to ridges 127 or 130. Each of the ridges may protrude from the surface of the third wall 106. As an alternative to or for use in combination with such ridges, the third wall 106 may include a textured region.

Referring now to FIGS. 2, 4 and 6, the second wall 125 and/or third wall portion 106 may, for example, include a step-down portion 121 where the second and/or third wall portion 125, 106 decreases in thickness in a region of the dampening device closer to the first wall portion 102. See also end view of FIG. 10.

The fourth and/or fifth wall portion 120, 124 may also include a step-up portion 134 (FIGS. 3, 5, 8, 9, and 10) where a fourth and/or fifth wall portion 120, 124 increases in thickness. The fourth and/or fifth wall 120, 124 may also include a plurality of ridges 122, 127. Each of the ridges may protrude from the surface of the corresponding wall 120, 124. As an alternative or for use in combination with such ridges, the third and/or fourth wall 120, 124 may include a textured region (not shown).

Referring now to FIG. 10, the sixth wall portion 104 may have a surface extending longitudinally at least partially in a plane substantially perpendicular to planes lying in longitudinally extending surfaces of the second wall portion 125, the third wall portion 106, the fourth wall portion 120, and the fifth wall portion 124. The sixth wall portion 104 may also have a surface extending longitudinally in a plane substantially parallel to a plane lying in a longitudinally extending surface of the first wall portion 102. The sixth wall portion 104 may optionally include an opening 105 though which a back end of the biopsy device 100 is uncovered when the dampening device 101 is installed on the biopsy device 100. Since a user may desire to use the sixth wall portion 23 of the biopsy device as a portion to place the user's thumb, for example, in order to provide leverage to pull the load device extensions 50a and/or 50b (e.g., with the user's finger or fingers), the opening 105 may be provided on the dampening device so as to not excessively increase the linear distance between the loading device extension 50a and/or 50b and the sixth wall portion 23 of the biopsy device when the dampening device is operated by the user's hand, for example.

Referring now to FIGS. 11-15, as an alternative to the abovementioned removal of the biopsy device from the dampening device though an opening, the dampening device may include a tear open portion 152 for allowing a user of the biopsy device to quickly remove the dampening apparatus 101 from the external surface of the biopsy device 100. The tear open portion 152 may allow a user to remove the dampening device by destructively tearing open a region of the flexible sleeve. The tear-open portion may be located on any of the abovementioned wall portions 102, 104, 106, 120, 124, 125, of the dampening device 101. In one example, the second wall portion 125 may include a tear open portion 152 terminating in a tab portion 150. The tab portion 150 may have a surface extending in a longitudinal direction within a plane substantially perpendicular to the plane falling within a longitudinally extending surface of the second wall 125 so as to form a smooth surface with second wall 125 when in an unused state. As an alternative, the tab portion 150 may have a surface extending in a longitudinal direction within a plane in a direction forming an angle (not shown) with the plane falling within a longitudinally extending surface of the wall 125 so as to protrude from the surface of the second wall 125 when in an unused state to improve a user's ability to grasp the tab portion 150. Further the tab portion 150 may include a textured surface, for example, to assist a user in grasping the tab portion 150. The tear open portion 152 may have a reduced thickness and/or may include perforations to form a path along a boundary of the tab portion 150, along which the flexible sleeve of the dampening device will more easily tear. The tear open portion 152 may connect to opening 107 on the first wall portion 102 through a region 153 so as to allow a user to tear open a region from the tab 150 to opening 107.

Figure 17:
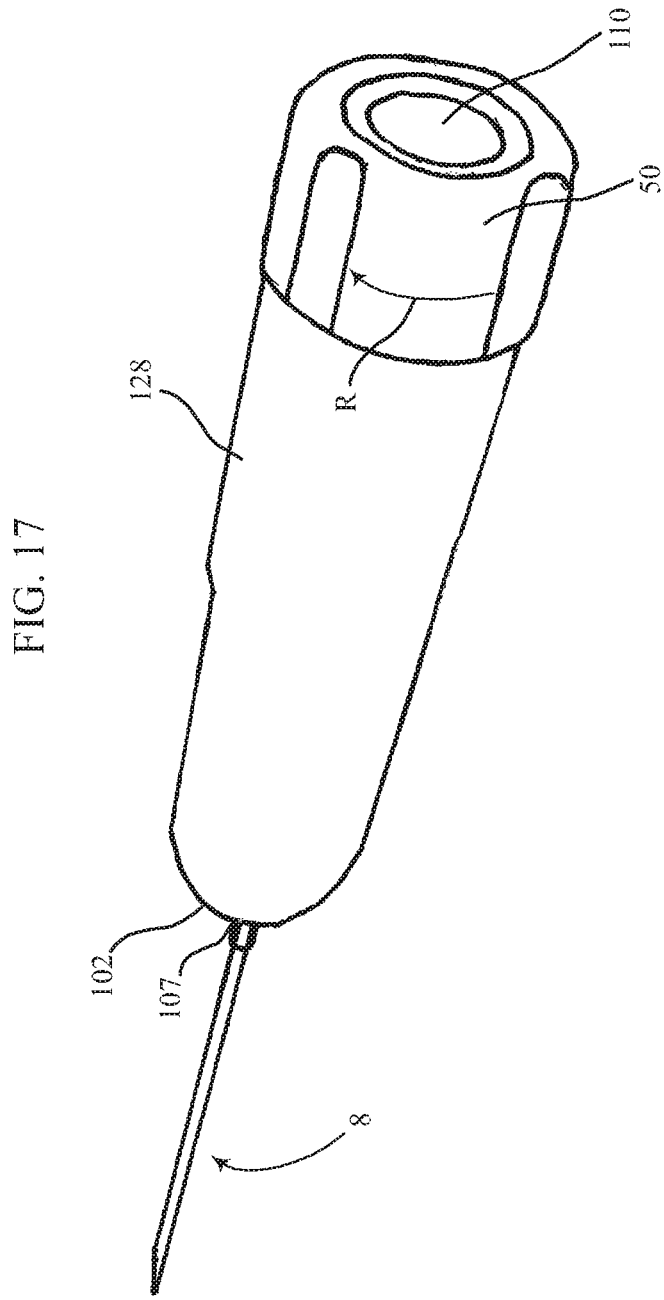
FIG. 17 is another perspective view depicting an example biopsy device having a dampening device installed in accordance with one aspect of the present disclosure.

Referring now to FIG. 17, as an example, the abovementioned damping device may be formed to correspond to a biopsy device having a rotatable loading portion 50 which may rotate in a direction R to load the biopsy device. The biopsy device may include a button 110 for triggering any of the abovementioned functions of the biopsy device (e.g., as described in conjunction with FIGS. 1-15). The dampening device may include a first wall portion 102 having an opening 107 for allowing a biopsy needle 8 to pass therethrough. The dampening device may include a wall portion 128 extending from the abovementioned first wall portion 102, the wall portion 128 having a generally conical shape for surrounding the corresponding outer surface of the biopsy device housing. Alternatively, for example, the curved wall portion 128 may be substantially cylindrically shaped and have an axis of extension parallel to or coaxial with an axis of extension of the needle 8. The substantially cylindrically or conically shaped curved wall portion 128 may further be formed to at least partially enclose a biopsy device and/or to extend from the first wall portion 128 to the rotatable loading portion 50.

Any of the abovementioned dampening devices may include selected portions of the abovementioned wall portions, for example as separate sleeves, molded to or bonded to the outer surface of the biopsy device, and may have selected openings or other features for selectively uncovering portions of the biopsy device, as desired. For instance, the damping device may include any number of openings corresponding to visual indicia (e.g. a portion indicating the spring in a biopsy device is loaded) or corresponding to any labeling or instructions on the biopsy device.

It is noted that the abovementioned damping devices are not limited to use with the structures described above and the openings therein; accordingly, the abovementioned dampening devices may be formed to conform in shape to, and at least partially enclose, any selected features of the outer surface of various types and shapes of biopsy devices. For example, a damping device may be formed so as to encapsulate only a certain portion of the biopsy device 100 shown in FIG. 1. The portion of the biopsy device 100 covered by the damping device may include, for example, only the surfaces 22, 23, and 24, leaving all or most of surfaces 21 and 25 of the biopsy device 100 uncovered. This partial covering approach may sufficiently dampen noise without unduly interfering with operation of the biopsy device 100.

Figure 18:
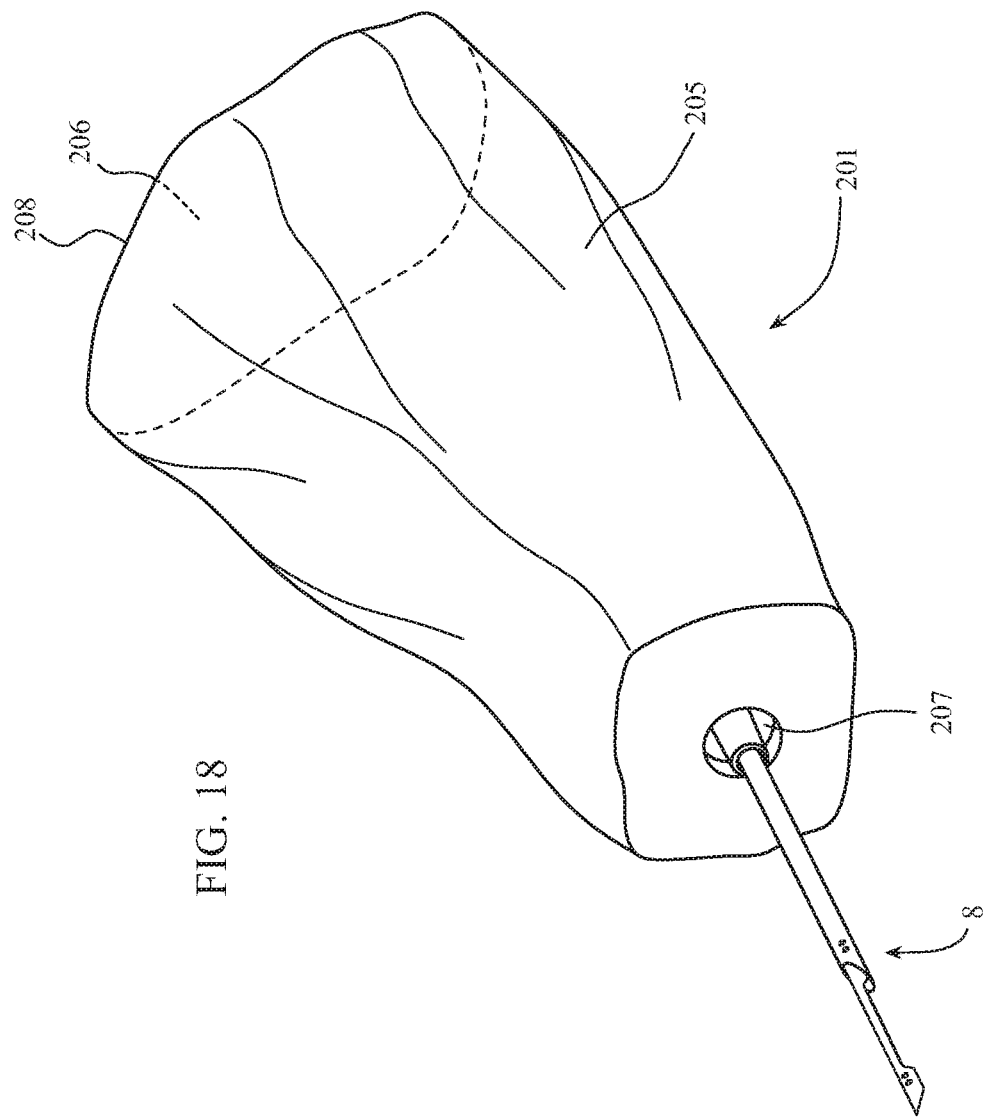
FIG. 18 is a prospective close up view depicting certain features of an example of a biopsy device having a dampening device installed in accordance with another aspect of the disclosure.

Referring now to FIG. 18, in another aspect of the disclosure, the dampening device 201 may include an elastic body portion having an outer surface 205 and an inner surface 206. The dampening device 201 may further include an opening 207 for allowing a biopsy needle 8 to pass through. The dampening device may include an opening 208 for allowing an object, such as a portion of a user's hand, to fit within the dampening device. The elastic body portion of the dampening device 201 may be sufficiently sized such that a user can operate any of the loading device extension, recessed loading portion, rotatable loading portion, cocking pullback portion or any triggers and/or controls associated with the biopsy device inside the dampening device 201. Further the elastic body portion may further be provided to loosely fit over the biopsy device such that a user can operate any of the abovementioned provisions of the biopsy device from an outer surface 205 of the elastic body. The aforementioned elastic body portion may further be tied or provided with a tying portion to enclose and substantially seal-off the opening 208.

In another aspect of the disclosure, usable with or alternatively to other aspects described herein, a spring constant or spring property of the springs used in the biopsy device may be altered to decrease the force applied when the device is fired. The decrease in force may be provided through the use of a biasing member with a decreased potential energy. As a non-limiting example, in abovementioned U.S. Pat. No. 5,951,489 (US '489), any of springs 64, 45, 55 and/or 70 may be replaced by a spring having a decreased spring constant. See US '489, FIGS. 7-16. The decreased spring constant and potential energy of the spring may result in a decrease in vibration and sound emitted from the biopsy device. Generally the potential energy of a spring may be expressed by U in the following equation (Formula 2):

$$U = \frac{1}{2}kx^2 \quad \text{(Formula 2)}$$

Where k is the spring force constant and x is the distance from equilibrium. By decreasing the spring force constant, a decrease in potential energy and accordingly a decrease in vibration and sound emitted by the biopsy device associated with a decreased release force may result. However, excessive decrease in spring force may result in a decreased ability of the stylet and/or cannula to penetrate tissue. As such, a progressive spring may be employed to slow the release force at a portion of the stroke known to cause the most vibration. For instance the force may be reduced at a beginning, end, or along central portion of the stroke.

Figure 19:
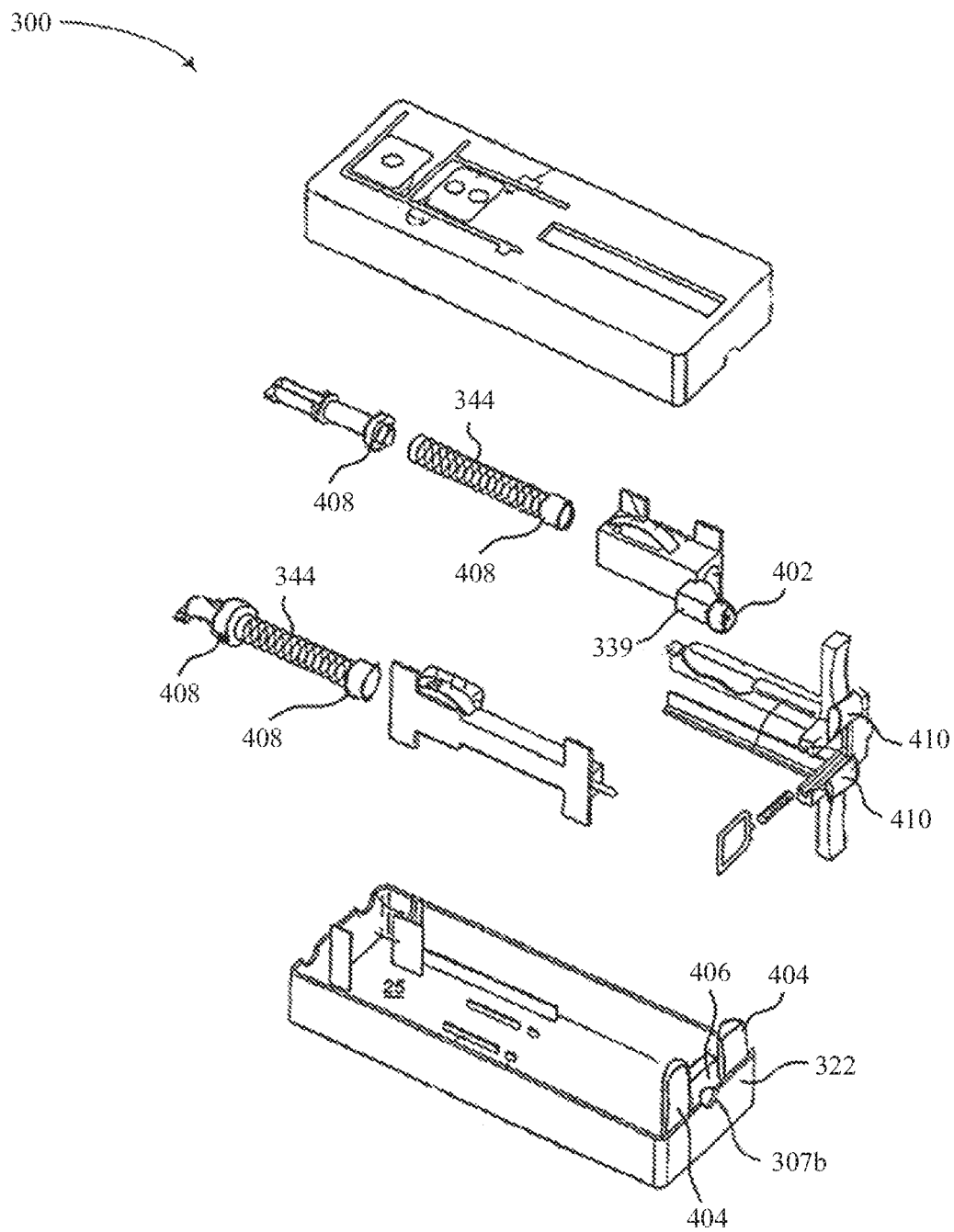
FIG. 19 is an exploded view of an example biopsy device having dampening devices installed in accordance with another aspect of the disclosure.

In accordance with another aspect of the disclosure, usable with or alternatively to other aspects described herein, a device and method may be employed for dampening a biopsy device internally using an elastic damper. An elastic damper may be added to the end portions of any biasing members that may be used in the biopsy device. In one non-limiting example, in abovementioned U.S. Pat. No. 5,951,489 any of springs 64, 45, 55 and/or 70 may include an elastic damper on either a single or both end portions. See US '489, FIGS. 7-16. Referring now to FIG. 19, the internal components of an example biopsy device 300 may include a cannula slider head portion 339, which may include an opening (not shown) for mounting a cannula (not shown). A cannula bumper or elastic portion 402 may be added to dampen and/or prevent contact between the cannula and/or cannula head portion 339 and a first wall 322 of the biopsy device. Further, a wall bumper or wall bumpers 404 may be attached to or placed at an inner surface of the front wall portion 322 of the biopsy device. A needle opening bumper portion 406 may be placed at a needle opening 307*b* of the biopsy device. The needle opening bumper portion 406, may include an opening proximate to opening 307*b* for allowing a biopsy needle to pass therethrough. A biasing member bumper or bumpers 408 may be located at either or both of the ends of any of the biasing members 344 or 364, for example. Further an elastic damper may be added between the coils as an alternative to or in combination with the abovementioned dampers to any one of or all of the springs. Elastic dampers may further be added to any moving portion of the biopsy device known to come in to contact with another portion of the biopsy device during operation. For example, the cannula slider 31 or stylet slider 33 in the '489 patent may include an elastic damper on the surfaces contacting any internal components during operation of the biopsy device. See US '489, FIG. 1A. The materials of construction of such elastic dampers may be similar to the materials used for forming the dampening apparatus 101 described in conjunction with FIGS. 1-15. The abovementioned bumpers or elastic dampers may be further include or in the alternative be formed of a foam, such as a polyethylene foam, reticulated polyurethane foam, a melamine foam, vinyl sponge, neoprene sponge, sponge rubber, vinyl nitrile and viscoelastic for example. The abovementioned bumpers or elastic members may further or in the alternative be formed of a rubber or other vibration reducing material. It is noted that the abovementioned bumpers and elastic dampers may be used in combination with or in lieu of any of the abovementioned external elastic damping sleeves or portions.

In yet another variation, elastic material may be emplaced or formed on other surfaces internal to the biopsy device, such as the inner surface of walls 22, 23, 24, and 25 of the device 100 of FIG. 1, so as to thereby dampen noise produced by operation of the device 100. The abovementioned elastic materials, foams and/or sponges may be used to form baffles on any one of the internal surfaces of the biopsy device to disrupt standing waves or adjust the frequency profile of any vibrations within the biopsy device.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

KEY FOR FIGURES

Reference Part Name
8 Needle
21 Third wall
22 First wall
23 Sixth wall
24 Fourth wall
25 Second wall
27 Fifth wall
50a Loading device extension
50b Loading device extension
68 Stylet
70 Springs
80 Cannula
90 Sliding channel
95 Channel
100 Biopsy device
101 Dampening device
102 First wall
104 Sixth wall portion
105 Opening
106 Third wall portion
107 Opening
110 First trigger
111 Second trigger
112 Narrowed width portion
114 Second opening
116 Abovementioned opening
117 Thickness
118 Opening
120 Fourth wall portion
121 Step-down portion
122 Ridges
124 Fifth wall portion
125 Second wall portion
127 Ridges
128 Curved wall portion
130 Ridges
134 Step-up portion
150 Tab
152 Tear open portion
153 Region
201 Dampening device
205 Outer surface
206 Inner surface
207 Opening
208 Opening
300 Biopsy device
307b Needle opening
322 First wall
339 Cannula slider head portion
344 Biasing members
400 Phon curves
402 Cannula bumper portion
404 Wall bumper portion
406 Needle opening bumper portion
408 Biasing member bumper
410 Loading device bumper

What is claimed is:

1. An elastic sleeve for dampening sound emitted from a biopsy device comprising:
an outer body portion, comprised of an elastic material having a thickness, the outer body portion being shaped to at least partially enclose the biopsy device, the outer body portion including;
a first wall portion having a surface extending at least partially within a first plane and having an opening for allowing a needle to pass through,
a second wall portion having a surface extending at least partially within a second plane, the second plane being substantially perpendicular to the first plane;
wherein the second wall portion has an opening for allowing a first loading device to pass therethrough, and
wherein the opening in the second wall portion is shaped and positioned to correspond to a sliding opening of the biopsy device when the biopsy device is enclosed by the sleeve; and
a third wall portion having a surface extending at least partially within a third plane, the third plane being substantially perpendicular to the first plane and substantially parallel to the second plane,
wherein the third wall portion has an opening for allowing a second loading device to pass through,
wherein the opening in the second wall portion and the opening in the third wall portion each comprise an elongate distal portion,
wherein a shape of the elongate distal portion of the opening in the second wall portion is substantially the same as a shape of the elongate distal portion of the opening in the third wall portion, and
where the opening in the third wall portion comprises a proximal portion that is in communication with the elongate distal portion of the third portion, and
wherein the proximal portion is configured to receive a trigger of the biopsy device.

2. The elastic sleeve of claim 1, the outer body portion further comprising:
a fourth wall portion having a surface extending at least partially within a fourth plane, the fourth plane being substantially perpendicular to each one of the first plane, the second plane and the third plane;
a fifth wall portion having a surface extending at least partially within a fifth plane, the fifth plane being perpendicular to each one of the first plane, the second plane and the third plane, wherein the fifth plane is substantially parallel to the fourth plane.

3. The elastic sleeve of claim 2, the outer body portion further comprising:
a sixth wall portion, wherein the sixth wall portion has a surface extending at least partially within a sixth plane, the sixth plane being substantially perpendicular to each one of the second plane, the third plane, the fourth plane and the fifth plane; wherein the sixth plane is substantially parallel to the first plane.

4. The elastic sleeve of claim 3, wherein the sixth wall portion has an opening.

5. The elastic sleeve of claim 1, the outer body portion further comprising a tear-open region, the tear-open region comprising:
a tab portion located on one of the second or third wall portions;
a tear open portion, having a boundary of reduced thickness, extending from said second or third side wall portion to the first wall opening, wherein the tear-open region is configured to be opened when a force is received by the tab portion.

6. The elastic sleeve of claim 2, wherein the fourth wall portion includes a plurality of ridges.

7. The elastic sleeve of claim 6, wherein the fifth wall portion includes a plurality of ridges.

8. The elastic sleeve of claim 2, wherein any one of said wall portions includes a textured portion.

9. The elastic sleeve of claim 1, wherein the third wall portion opening includes an extended rectangular opening for allowing at least one trigger of the biopsy device to pass through.

10. The elastic sleeve of claim 1, wherein at least one of the second and third side wall portions includes a plurality of ridges.

11. The elastic sleeve of claim 1, wherein the elastic sleeve is configured to dampen vibrations emitted from the biopsy device from a range of 3,000 to 4,000 Hz.

12. An elastic sleeve for dampening sound emitted from a biopsy device comprising:
    an outer body portion, comprised of an elastic material having a thickness, the outer body portion being shaped to at least partially enclose an inner space, the outer body portion including;
        a first wall portion having a surface extending on a first plane and having a first opening;
        a second wall portion having a surface extending at least partially within a second plane, the second plane intersecting at an angle with the first plane;
        a third wall portion, having a surface extending at least partially on a third plane, the third plane being separate from each one of the first plane and second plane, and the third plane intersecting at an angle with the first plane; and
        a tear-open region, the tear-open region comprising:
            a tab portion located on at least one of the second or third wall portions;
            a tear-open portion, having a boundary of reduced thickness,
            extending from a second opening to the first opening,
        wherein the second opening is entirely enclosed by the second wall portion or the third wall portion,
        wherein the tear-open region is configured to be opened when a force is received by the tab portion,
        wherein the second opening comprises a proximal portion that is in communication with an elongate distal portion,
        wherein the proximal portion is configured to receive a trigger of the biopsy device, and
        wherein a loader device of the biopsy device is configured to pass through the distal portion.

13. A system for dampening sound emitted from a biopsy device comprising:
    a biopsy device having a cylindrical needle extending away from the biopsy device; and
    an elastic sleeve for the biopsy device comprising:
        an outer body portion, comprised of an elastic material having a thickness, the outer body portion being shaped to at least partially enclose the biopsy device, the outer body portion including a first opening extending through a first wall portion, the first opening positioned for allowing the needle of the biopsy device to pass therethrough;
        a second wall portion having a surface extending at least partially within a second plane, the second plane being substantially perpendicular to the first wall portion and having an opening for allowing a first loading device extension to pass through, wherein the opening is shaped and positioned to correspond to a sliding opening of the biopsy device when the biopsy device is enclosed by the elastic sleeve; and
        a third wall portion having a surface extending at least partially within a third plane, the third plane being substantially perpendicular to the first plane and substantially parallel to the second plane,
    wherein the first opening is round to correspond to the cylindrical needle,
    wherein the outer body portion thereby dampens sound emitted from the biopsy device, and
    wherein the first wall portion surrounds the first opening and has a surface extending at least partially within a first plane.

14. The system of claim 13, wherein the outer body portion further comprises:
    a second wall portion having a surface extending from the first wall portion, the second wall portion having a substantially cylindrical or conical outer surface shape.

15. The system of claim 13, wherein the elastic sleeve is configured to dampen vibrations emitted from the biopsy device from 2,000 to 5,000 Hz.

16. A method for dampening sound emitted from a biopsy device, the method comprising:
    encapsulating the biopsy device with a sleeve having an outer body portion, the outer body portion comprising an elastic material having a thickness, the outer body portion further including:
        a first wall portion having a surface extending at least partially within a first plane and having an opening for allowing a needle to pass through,
        a second wall portion having a surface extending at least partially within a second plane, the second plane being substantially perpendicular to the first wall portion and having an opening for allowing first loading device extension to pass through, wherein the opening in the second wall portion is entirely enclosed by the second wall portion; and
        a third wall portion having a surface extending at least partially within a third plane, the third plane being substantially perpendicular to the first plane and substantially parallel to the second plane; and
    providing a tear-open region, the tear-open region comprising:
        a tab portion located on one of the second or third wall portions; and
        a tear open portion, having a boundary of reduced thickness, extending from said second or third side wall portion to the first wall opening, wherein the tear-open region is provided so as to be opened when a force is received by the tab portion.

17. The method of claim 16, wherein the third wall portion further includes an opening for allowing a second loading device extension to pass through.

18. The method of claim 16, wherein the thickness of the elastic material varies within the outer body portion.

19. The method of claim 16, wherein the elastic sleeve is configured to dampen vibrations emitted from the biopsy device from a range of 3,000 to 4,000 Hz.

* * * * *